(12) United States Patent
Ding et al.

(10) Patent No.: US 7,869,873 B2
(45) Date of Patent: Jan. 11, 2011

(54) METHOD AND SYSTEM FOR SETTING CARDIAC RESYNCHRONIZATION THERAPY PARAMETERS

(75) Inventors: Jiang Ding, Maplewood, MN (US);
Yinghong Yu, Maplewood, MN (US);
Bruce H. KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 822 days.

(21) Appl. No.: 11/681,244

(22) Filed: Mar. 2, 2007

(65) Prior Publication Data

US 2007/0150013 A1 Jun. 28, 2007

Related U.S. Application Data

(62) Division of application No. 10/744,237, filed on Dec. 22, 2003, now Pat. No. 7,203,540.

(51) Int. Cl.
*A61N 1/00* (2006.01)
(52) U.S. Cl. .......................................................... 607/9
(58) Field of Classification Search ..................... 607/9, 607/11, 25
See application file for complete search history.

(56) References Cited

U.S. PATENT DOCUMENTS

| | | | |
|---|---|---|---|
| 3,937,226 A | 2/1976 | Funke |
| 4,088,140 A | 5/1978 | Rockland et al. |
| 4,332,259 A | 6/1982 | McCorkle, Jr. |
| 4,354,497 A | 10/1982 | Kahn |
| 4,428,378 A | 1/1984 | Anderson et al. |
| 4,458,677 A | 7/1984 | McCorkle, Jr. |
| 4,543,963 A | 10/1985 | Gessman |
| 4,548,203 A | 10/1985 | Tacker, Jr. et al. |
| 4,856,524 A | 8/1989 | Baker, Jr. |
| 4,928,688 A | 5/1990 | Mower |
| 4,972,834 A | 11/1990 | Begemann et al. |
| 5,052,388 A | 10/1991 | Sivula et al. |
| 5,174,289 A | 12/1992 | Cohen |
| 5,179,949 A | 1/1993 | Chirife |
| 5,190,035 A | 3/1993 | Salo et al. |
| 5,267,560 A | 12/1993 | Cohen |

(Continued)

OTHER PUBLICATIONS

U.S. Appl. No. 10/744,237, filed Dec. 22, 2003, Method and System for Setting Cardiac Resynchronization Therapy Parameters.

(Continued)

*Primary Examiner*—George Manuel
(74) *Attorney, Agent, or Firm*—Schwegman, Lundberg & Woessner, P.A.

(57) ABSTRACT

A method or system for computing and/or setting optimal cardiac resynchronization pacing parameters as derived from intrinsic conduction data is presented. The intrinsic conduction data includes intrinsic atrio-ventricular and interventricular delay intervals which may be collected via the sensing channels of an implantable cardiac device. Among the parameters which may be optimized in this manner are an atrioventricular delay interval and a biventricular offset interval. In one of its aspects, the invention provides for computing optimum pacing parameters for patients having some degree of AV block or with atrial conduction deficits. Another aspect of the invention relates to a pacing mode and configuration for providing cardiac resynchronization therapy to patients with a right ventricular conduction disorder.

14 Claims, 3 Drawing Sheets

U.S. PATENT DOCUMENTS

| | | | |
|---|---|---|---|
| 5,282,838 | A | 2/1994 | Hauser et al. |
| 5,331,966 | A | 7/1994 | Bennett et al. |
| 5,403,356 | A | 4/1995 | Hill et al. |
| 5,417,714 | A | 5/1995 | Levine et al. |
| 5,466,245 | A | 11/1995 | Spinelli et al. |
| 5,507,782 | A | 4/1996 | Kieval et al. |
| 5,507,784 | A | 4/1996 | Hill et al. |
| 5,514,161 | A | 5/1996 | Limousin |
| 5,514,163 | A | 5/1996 | Markowitz et al. |
| 5,527,347 | A | 6/1996 | Shelton et al. |
| 5,626,620 | A | 5/1997 | Kieval et al. |
| 5,626,623 | A | 5/1997 | Kieval et al. |
| 5,643,327 | A | 7/1997 | Dawson et al. |
| 5,674,259 | A | 10/1997 | Gray |
| 5,716,383 | A | 2/1998 | Kieval et al. |
| 5,720,768 | A | 2/1998 | Verboven-Nelissen |
| 5,749,906 | A | 5/1998 | Kieval et al. |
| 5,792,203 | A | 8/1998 | Schroeppel |
| 5,797,970 | A | 8/1998 | Pouvreau |
| 5,800,471 | A | 9/1998 | Baumann |
| 5,861,007 | A | 1/1999 | Hess et al. |
| 5,873,895 | A | 2/1999 | Sholder et al. |
| 5,902,324 | A | 5/1999 | Thompson et al. |
| 6,058,328 | A | 5/2000 | Levine et al. |
| 6,070,100 | A | 5/2000 | Bakels et al. |
| 6,081,747 | A | 6/2000 | Levine et al. |
| 6,129,744 | A | 10/2000 | Boute |
| 6,141,586 | A | 10/2000 | Mower |
| 6,144,880 | A | 11/2000 | Ding et al. |
| 6,161,042 | A | 12/2000 | Hartley et al. |
| 6,167,307 | A | 12/2000 | Hess |
| 6,208,901 | B1 | 3/2001 | Hartung |
| 6,219,579 | B1 | 4/2001 | Bakels et al. |
| 6,311,088 | B1 | 10/2001 | Betzold et al. |
| 6,351,673 | B1 | 2/2002 | Ding et al. |
| 6,360,127 | B1 | 3/2002 | Ding et al. |
| 6,498,949 | B2 | 12/2002 | Levine et al. |
| 6,507,756 | B1 | 1/2003 | Heynen et al. |
| 6,542,775 | B2 | 4/2003 | Ding et al. |
| 6,567,700 | B1 * | 5/2003 | Turcott et al. .................. 607/9 |
| 6,597,951 | B2 | 7/2003 | Kramer et al. |
| 6,604,000 | B2 | 8/2003 | Lu |
| 6,654,637 | B2 | 11/2003 | Rouw et al. |
| 6,684,103 | B2 | 1/2004 | Ding et al. |
| 6,751,504 | B2 | 6/2004 | Fishler |
| 6,792,307 | B1 | 9/2004 | Levine et al. |
| 6,792,308 | B2 | 9/2004 | Corbucci |
| 6,804,555 | B2 | 10/2004 | Warkentin |
| 6,856,836 | B2 | 2/2005 | Ding et al. |
| 6,859,665 | B2 | 2/2005 | Ding et al. |
| 6,871,096 | B2 | 3/2005 | Hill |
| 6,882,882 | B2 | 4/2005 | Struble et al. |
| 6,937,895 | B1 | 8/2005 | Lu |
| 6,947,794 | B1 | 9/2005 | Levine |
| 7,013,176 | B2 | 3/2006 | Ding et al. |
| 7,020,522 | B1 | 3/2006 | Hoijer et al. |
| 7,020,524 | B1 | 3/2006 | Bradley |
| 7,047,073 | B2 | 5/2006 | Hoijer et al. |
| 7,065,406 | B1 | 6/2006 | Gustavsson |
| 7,069,079 | B2 | 6/2006 | Struble et al. |
| 7,079,895 | B2 | 7/2006 | Verbeek et al. |
| 7,079,896 | B1 | 7/2006 | Park et al. |
| 7,110,817 | B2 | 9/2006 | Yu et al. |
| 7,123,960 | B2 | 10/2006 | Ding et al. |
| 7,142,922 | B2 | 11/2006 | Spinelli et al. |
| 7,158,830 | B2 | 1/2007 | Yu et al. |
| 7,177,687 | B2 | 2/2007 | Schuller |
| 7,184,835 | B2 | 2/2007 | Kramer et al. |
| 7,203,540 | B2 | 4/2007 | Ding et al. |
| 7,215,998 | B2 | 5/2007 | Wesselink et al. |
| 7,228,174 | B2 | 6/2007 | Burnes et al. |
| 7,236,824 | B2 | 6/2007 | Rouw et al. |
| 7,239,915 | B2 | 7/2007 | Cohen |
| 7,245,969 | B2 | 7/2007 | Lincoln et al. |
| 7,248,925 | B2 | 7/2007 | Bruhns et al. |
| 7,389,141 | B2 | 6/2008 | Hall et al. |
| 7,613,514 | B2 | 11/2009 | Fogoros et al. |
| 7,630,764 | B2 | 12/2009 | Ding et al. |
| 2003/0078628 | A1 | 4/2003 | Holmstrom et al. |
| 2003/0105496 | A1 | 6/2003 | Yu et al. |
| 2003/0130702 | A1 | 7/2003 | Kramer et al. |
| 2003/0144702 | A1 | 7/2003 | Yu et al. |
| 2003/0144703 | A1 | 7/2003 | Yu et al. |
| 2004/0024423 | A1 | 2/2004 | Lincoln et al. |
| 2004/0030356 | A1 | 2/2004 | Osypka et al. |
| 2004/0147966 | A1 | 7/2004 | Ding et al. |
| 2004/0215258 | A1 | 10/2004 | Lovett et al. |
| 2005/0131472 | A1 | 6/2005 | Ding et al. |
| 2005/0137632 | A1 | 6/2005 | Ding et al. |
| 2005/0137634 | A1 | 6/2005 | Hall et al. |
| 2006/0047320 | A1 | 3/2006 | Ding et al. |

OTHER PUBLICATIONS

U.S. Appl. No. 10/920,698, filed Aug. 18, 2004, Biatrial Pacing Optimization for Biventricular Pacing.

U.S. Appl. No. 11/113,827, filed Apr. 25, 2005, Method and System for Treatment of Mechanical Cardiac Asynchrony.

U.S. Appl. No. 11/206,394, filed Aug. 18, 2005, Method and System for Delivering Cardiac Resynchronization Therapy with Variable Atrioventricular Delay.

Auricchio, Angelo , "Effect of pacing chamber and atrioventricular delay on acute systolic function of paced patients with congestive heart failure. The Pacing Therapies for Congestive Heart Failure Study Group. The Guidant Congestive Heart Failure Research Group", *Circulation*, 99(23). (Jun. 15, 1999),2993-3001.

Cazeau, S , et al., "Four chamber pacing in dilated cardiomyopathy", *Pacing and clinical electrophysiology : PACE*, 17(11 Pt 2), (Nov. 1994),1974-9.

Cochlain, et al., "The Effects of the Interval Between Right and Left Ventricular Activation on Sychronization in Patients with Bi-ventricular Pacemakers", *Pacing and clinical electrophysiology : PACE*, 23(11), (Apr. 2000),576.

Daubert, Claude , "Permanent dual atrium pacing in major interatrial conduction blocks: a four years experience (Abstract 141)", *Pacing and clinical electrophysiology : PACE*, 3(Part II), NASPE Abstracts—Abstract 141,(Apr. 1993),885.

Daubert, L. C., "Permanent Left Ventricular Pacing With Transvenous Leads Inserted Into the Coronary Veins", *Pacing and Clinical Electrophysiology : PACE*, 21, (Jan. 1998),239-245.

Daubert, Claude , "Renewal of permanent left atrial pacing via the coronary sinus", *Pacing and clinical electrophysiology : PACE*, 25(Part II), NASPE Abstracts—Abstract 255,(Apr. 1992),572.

Durrer, Dirk , et al., "Total excitation of the isolated human heart.", *Circulation*, 41(6), (Jun. 1970),899-912.

Hall, J. A., "Biatrial Pacing Optimization for Biventricular Pacing", U.S. Appl. No. 10/920,698. filed Aug. 18, 2004, 22 pgs.

Lieberman, Randy , et al., "Relationship Between Electrical and Hemodynamic Parameters Using Bi-Ventricular and Uni-Ventricular Pacing in Heart Failure Patients", *Journal of the American College of Cardiology*, (Feb. 2001),155A.

* cited by examiner

METHOD AND SYSTEM FOR SETTING CARDIAC RESYNCHRONIZATION THERAPY PARAMETERS

CROSS REFERENCE TO RELATED APPLICATION(S)

This application is a division of U.S. patent application Ser. No. 10/744,237, filed on Dec. 22, 2003, now U.S. Pat. No. 7,203,540, the specification of which is incorporated herein by reference.

FIELD OF THE INVENTION

This invention pertains to methods and apparatus for treating cardiac disease with electrical therapy.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction.

Pacing therapy can also be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. Heart failure can be due to a variety of etiologies with ischemic heart disease being the most common. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction and/or an atrial pace. Appropriate specification of these pacing parameters is necessary in order to achieve optimum improvement in cardiac function, and it is this problem with which the present invention is primarily concerned.

SUMMARY

The present invention relates to a method or system for computing and/or setting optimal cardiac resynchronization pacing parameters as derived from intrinsic conduction data. Such intrinsic conduction data may be collected via the sensing channels of an implantable cardiac device and either utilized by the implantable device itself to compute optimal pacing parameters or transmitted to an external programmer via a wireless telemetry link. In one of its aspects, the invention provides for computing optimum pacing parameters for patients having some degree of AV block or with atrial conduction deficits. Another aspect of the invention relates to a pacing mode and configuration for providing cardiac resynchronization therapy to patients with a right ventricular conduction disorder.

DETAILED DESCRIPTION

The present invention relates to a method or system for setting the pacing parameters and/or pacing configuration of a cardiac rhythm management device for delivering resynchronization pacing to the left ventricle (LV) and/or the right ventricle (RV) in order to compensate for ventricular conduction delays and improve the coordination of ventricular contractions. In accordance with the present invention, optimum pacing parameters may be computed based upon intrinsic conduction data derived from measurements of intra-cardiac conduction times using the sensing channels of an implanted device. Algorithms for computing and/or setting these pacing parameters may be implemented in either the programming of an external programmer, in the programming of the implanted device itself, or as a manually implemented procedure (e.g., by using a printed table lookup to compute optimum parameters from intrinsic conduction data). In one embodiment, the external programmer communicates with the implantable device over a telemetry link and receives either raw electrogram data, markers corresponding to particular sensed events, or measurements of the intervals between particular sensed events as computed by the implantable device. The external programmer may then compute optimal settings for pacing parameters which are either transmitted to the implantable device for immediate reprogramming or presented to a clinician operating the external programmer as recommendations. Alternatively, the external programmer may present the intrinsic conduction data to the clinician who then programs the implantable device in accordance with an algorithm. In another embodiment, the implantable device is programmed to automatically set certain pacing parameters in accordance with information gathered from its sensing channels.

As will be explained in more detail below, one aspect of the present invention involves the computation based upon intrinsic conduction data of an optimum atrio-ventricular delay (AVD) interval for delivering ventricular resynchronization therapy in an atrial tracking and/or atrio-ventricular sequential pacing mode to patients having some degree of AV block or having an atrial conduction delay. Another aspect relates to the optimal pacing configuration for delivering ventricular resynchronization therapy to patients having a right ventricular conduction deficit.

1. Exemplary Hardware Platform

Figure 1:
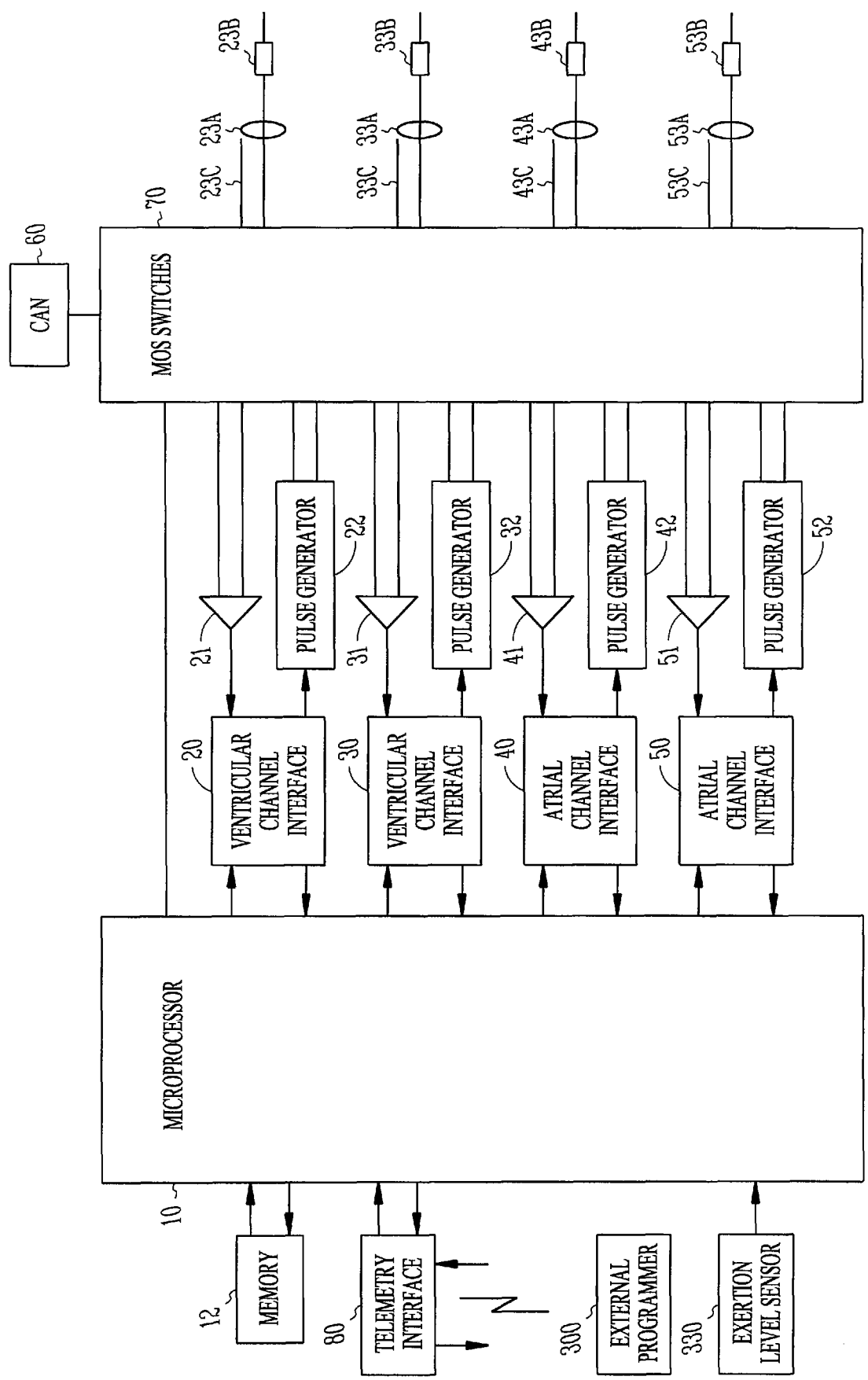
FIG. 1 is a system diagram of exemplary hardware components for delivering cardiac resynchronization therapy.

The following is a description of exemplary hardware components used for practicing the present invention. A block diagram of an implantable cardiac rhythm management device or pulse generator having multiple sensing and pacing channels is shown in FIG. 1. Pacing of the heart with an implanted device involves excitatory electrical stimulation of the heart by the delivery of pacing pulses to an electrode in electrical contact with the myocardium. The device is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

The controller of the device in FIG. 1 is made up of a microprocessor 10 communicating with a memory 12 via a bidirectional data bus, where the memory 12 typically comprises a ROM (read-only memory) and, or a RAM (random-access memory). The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller is capable of operating the pacemaker in a number of programmed modes where a programmed mode defines how pacing pulses are output in response to sensed events and expiration of time intervals. A telemetry interface 80 is provided for communicating with an external programmer 300. The external programmer is a computerized device with an associated display and input means that can interrogate the pacemaker and receive stored data as well as directly adjust the operating parameters of the pacemaker. As described below, in certain embodiments of a system for setting pacing parameters, the external programmer may be utilized for computing optimal pacing parameters from data received from the implantable device over the telemetry link which can then be set automatically or presented to a clinician in the form of recommendations.

The embodiment shown in FIG. 1 has four sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing with or without atrial tracking, biventricular pacing, or multi-site pacing of a single chamber. In an example configuration, a left atrial sensing/pacing channel includes ring electrode 53A and tip electrode 53B of bipolar lead 53C, sense amplifier 51, pulse generator 52, and a channel interface 50, and a right atrial sensing/pacing channel includes ring electrode 43A and tip electrode 43B of bipolar lead 43C, sense amplifier 41, pulse generator 42, and a channel interface 40. A right ventricular sensing/pacing channel includes ring electrode 23A and tip electrode 23B of bipolar lead 23C, sense amplifier 21, pulse generator 22, and a channel interface 20, and a left ventricular sensing/pacing channel includes ring electrode 33A and tip electrode 33B of bipolar lead 33C, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels and controls the delivery of paces in accordance with a pacing mode. An exertion level sensor 330 (e.g., an accelerometer, a minute ventilation sensor, or other sensor that measures a parameter related to metabolic demand) enables the controller to adapt the atrial and/or ventricular pacing rate in accordance with changes in the patient's physical activity, termed a rate-adaptive pacing mode. The sensing circuitry of the device generates atrial and ventricular electrogram signals from the voltages sensed by the electrodes of a particular channel. An electrogram is analogous to a surface EKG and indicates the time course and amplitude of cardiac depolarization and repolarization that occurs during either an intrinsic or paced beat. When an electrogram signal in an atrial or ventricular sensing channel exceeds a specified threshold, the controller detects an atrial or ventricular sense, respectively, which pacing algorithms may employ to trigger or inhibit pacing.

2. Cardiac Resynchronization Pacing Therapy

Cardiac resynchronization therapy is most conveniently delivered in conjunction with a bradycardia pacing mode. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the atrio-ventricular pacing delay interval or AVD, where a ventricular pacing pulse is delivered upon expiration of the atrio-ventricular pacing delay interval if no ventricular sense occurs before. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that an AVD starts with either an atrial pace or sense. When used in CRT, the AVD may be the same or different in the cases of atrial tracking and AV sequential pacing.

As described above, cardiac resynchronization therapy is pacing stimulation applied to one or more heart chambers in a manner that compensates for conduction delays. Ventricular resynchronization pacing is useful in treating heart failure in patients with interventricular or intraventricular conduction defects because, although not directly inotropic, resynchronization results in a more coordinated contraction of the ventricles with improved pumping efficiency and increased cardiac output. Ventricular resynchronization can be achieved in certain patients by pacing at a single unconventional site, such as the left ventricle instead of the right ventricle in patients with left ventricular conduction defects. Resynchronization pacing may also involve biventricular pacing with the paces to right and left ventricles delivered either simultaneously or sequentially, with the interval between the paces termed the biventricular offset (BVO) interval (also sometimes referred to as the LV offset (LVO) interval or VV delay). The offset interval may be zero in order to pace both ventricles simultaneously, or non-zero in order to pace the left and right ventricles sequentially. As the term is used herein, a negative BVO refers to pacing the left ventricle before the right, while a positive BVO refers to pacing the right ventricle first. In an example biventricular resynchronization pacing mode, right atrial paces and senses trigger an AVD interval which upon expiration results in a pace to one of the ventricles and which is stopped by a right ventricular sense. The contralateral ventricular pace is delivered at the specified BVO interval with respect to expiration of the AVD interval.

Cardiac resynchronization therapy is most commonly applied in the treatment of patients with heart failure due to left ventricular dysfunction which is either caused by or contributed to by left ventricular conduction abnormalities. In such patients, the left ventricle or parts of the left ventricle contract later than normal during systole which thereby impairs pumping efficiency. In order to resynchronize ventricular contractions in such patients, pacing therapy is applied such that the left ventricle or a portion of the left ventricle is pre-excited relative to when it would become depolarized in an intrinsic contraction. Optimal pre-excitation of the left ventricle in a given patient may be obtained with biventricular pacing or with left ventricular-only pacing. Although not as common, some patients have a right ventricular conduction deficit such as right bundle branch block and require pre-excitation of the right ventricle in order achieve synchronization of their ventricular contractions.

3. Optimal Adjustment of Pre-excitation Timing Parameters

Once a particular resynchronization pacing configuration and mode is selected for a patient, pacing parameters affecting the manner and extent to which pre-excitation is applied must be specified. For optimum hemodynamic performance, it is desirable to deliver ventricular pacing, whether for resynchronization pacing or conventional bradycardia pacing, in an atrial tracking and/or AV sequential pacing mode in order to maintain the function of the atria in pre-loading the ventricles (sometimes referred to atrio-ventricular synchrony). Since the objective of CRT is to improve a patient's cardiac pumping function, it is therefore normally delivered in an atrial-tracking and/or AV sequential mode and requires specification of AVD and BVO intervals which, ideally, result in the ventricles being synchronized during systole after being optimally preloaded during atrial systole. That is, both optimal interventricular synchrony and optimal atrio-ventricular synchrony are achieved. As the term is used herein for biventricular pacing, the AVD interval refers to the interval between an atrial event (i.e., a pace or sense in one of the atria, usually the right atrium) and the first ventricular pace which pre-excites one of the ventricles. The AVD interval may be the same or different depending upon whether it is initiated by an atrial sense or pace (i.e., in atrial tracking and AV sequential pacing modes, respectively), The pacing instant for the non-pre-excited ventricle is specified by the BVO interval so that it is paced at an interval AVD+BVO after the atrial event. It should be appreciated that specifying AVD and BVO intervals is the same as specifying a separate AVD interval for each ventricle, designated as AVDR for the right ventricle and AVDL for the left ventricle. In patients with intact and normally functioning AV conduction pathways, the non-pre-excited ventricle will be paced, if at all, close to the time at which that ventricle is intrinsically activated in order to achieve optimal preloading. In patients with normal AV conduction, the optimal AVD and BVO intervals are thus related to both the intrinsic atrio-ventricular interval and the amount of pre-excitation needed for one ventricle relative to the other (i.e., the extent of the ventricular conduction deficit).

In order to optimally specify the AVD and BVO parameters for a particular patient, clinical hemodynamic testing may be performed after implantation where the parameters are varied as cardiac function is assessed. For example, a patient may be given resynchronization stimulation while varying pre-excitation timing parameters in order to determine the values of the parameters that result in maximum cardiac performance, as determined by measuring a parameter reflective of cardiac function such as maximum left ventricular pressure change (dP/dt), arterial pulse pressure, or measurements of cardiac output. Determining optimal pacing parameters for an individual patient by clinical hemodynamic testing, however, is difficult and costly. It would be advantageous if such optimal pacing parameters could be determined from measurements of intrinsic conduction parameters which reflect how excitation is conducted within the patient's heart during intrinsic beats. In the approach of the present invention, therefore, intrinsic conduction data is collected from a surface EKG or from the sensing channels of the implantable cardiac resynchronization device and then used to compute optimum values of resynchronization pacing parameters.

As noted above, the objective of CRT is to restore a normal or near-normal conduction sequence to ventricular contractions by using pacing pulses to compensate for ventricular conduction deficits. CRT is most commonly used to treat left ventricular dysfunction brought about by parts of the left ventricle contracting later than normal during an intrinsic cardiac cycle. Biventricular (or left ventricle-only) pacing accomplishes this by pre-exciting the left ventricle with a first pace delivered to the left ventricle followed by a pace to the right ventricle at the BVO interval (or intrinsic activation of the right ventricle in the case of left ventricle-only pacing). The left ventricle electrode excites the left ventricular free wall, while the right ventricle electrode excites the ventricular septum. The desired situation is simultaneous contraction of the left ventricular free wall and septum (septum- free wall fusion). When clinical hemodynamic testing is performed on a population of subjects with intact AV pathways to determine the optimum values of the AVD and BVO intervals, there is found to be a correlation between the optimum AVD and BVO intervals for a particular subject and that subject's measured conduction delay between the right and left ventricles during an intrinsic beat. The optimum AVD interval and the intrinsic atrio-ventricular interval are also correlated from patient to patient. Therefore, the optimum AVD and BVO intervals for a particular patient may be estimated from intrinsic conduction data in terms of specified coefficients $k_n$ as:

$$BVO = k_1 \cdot \Delta_{RL} + k_2$$

and $$AVD = k_3 AV_R + k_3 \cdot \Delta_{RL} + k_4$$

where $\Delta_{RL}$ is a measurement reflective of the interventricular conduction delay between the right and left ventricles such as the interval between right and left ventricular senses or the QRS width on a surface ECG, and $AV_R$ is the right intrinsic atrio-ventricular interval measured as the interval between an atrial sense (or pace) and a right ventricular sense. It should be appreciated that these equations can also be expressed in terms of separate AVD intervals for the right and left ventricles, designated as AVDR and AVDL, respectively, and separate measured intrinsic atrio-ventricular intervals for the right and left ventricles, designated $AV_R$ and $AV_L$, respectively. The intervals are thus related as:

$$AV_R - AV_L = \Delta_{RL} \text{ (if determined by right and left ventricular senses)}$$

and $$AVDL - AVDR = BVO.$$

The equations for computing optimal values of AVDR and AVDL are thus:

$$AVDR = k_5 AV_R + k_6 AV_L + k_7$$

and $$AVDL = k_8 AV_R + k_9 AV_L + k_{10}.$$

In certain implementations of the techniques described herein, separate intrinsic atrio-ventricular intervals are measured following an atrial sense and following an atrial pace which are then used to compute AV delay intervals for pacing in atrial tracking and AV sequential modes, respectively. Also, unless otherwise specified, the term biventricular pacing should be taken to include left ventricle-only pacing. If the computed optimal BVO interval is a large negative value which is longer than the right intrinsic atrio-ventricular interval, the right ventricle will be activated intrinsically anyway so that the biventricular pacing is effectively left ventricle-only pacing.

In order to pre-derive the specified coefficients for later programming into the system or for use by a clinician, clinical population data is obtained that relates particular values of the measured intrinsic conduction parameters to an optimum value of the pre-excitation timing parameter as determined by concurrent measurement of another parameter reflective of cardiac function (e.g., maximum dP/dt or minimum atrial rate). A linear regression analysis is then performed to derive values of the specified coefficients used in the formula for setting the pre-excitation timing parameter, the specified coefficients thus being regression coefficients.

The techniques for setting resynchronization pacing parameters as described above, as well as others to be described below, may be implemented in a number of different ways. In one implementation, a system for setting the pacing parameters includes an external programmer. In an example embodiment, one or more intrinsic conduction parameters, as measured from electrogram signals generated by the sensing channels of an implantable cardiac resynchronization device during intrinsic beats, are transmitted to the external programmer via a wireless telemetry link. The measured intrinsic conduction parameters may represent averages of values obtained during a specified number of intrinsic beats. The external programmer then computes a pre-excitation timing parameter such as the AVD or BVO in accordance with a formula that equates an optimum value of the pre-excitation timing parameter to a linear sum of the measured intrinsic conduction parameters multiplied by specified coefficients. In an automated system, the external programmer then automatically programs the implantable device with the computed optimum parameter values, while in a semi-automated system the external programmer presents the computed optimum values to a clinician in the form of a recommendation. An automated system may also be made up of the implantable device alone which collects intrinsic conduction data, computes the optimum parameter values, and then sets the parameters accordingly. In another embodiment, which may be referred to as a manual system, the external programmer presents the collected intrinsic conduction data to a clinician who then programs the implantable device with parameters computed from the intrinsic conduction data by, for example, using a printed lookup table and procedure. Unless otherwise specified, references to a system for computing or setting pacing parameters throughout this document should be taken to include any of the automated, semi-automated, or manual systems just described.

4. Computation of Optimal Pacing Parameters Based upon Atrial Conduction Delay

The above-described methods for computing optimal resynchronization pacing parameters from intrinsic conduction data are based upon measured intrinsic conduction data which include intrinsic atrio-ventricular intervals and/or interventricular conduction delays. Another measurable intrinsic conduction value which may be used in computing optimal pacing parameters is the conduction delay between the right and left atria during an intrinsic beat. One use of this technique is to compute optimal resynchronization pacing parameters for patients with AV block. AV block refers to an impairment in the AV conduction pathways such that either no intrinsic conduction from the atria to the ventricles occurs (complete or $3^{rd}$ degree AV block) or the intrinsic atrio-ventricular interval is longer than normal. In patients with some degree of AV block, the above techniques cannot be used to estimate the optimum AVD interval for CRT because either no measured intrinsic atrio-ventricular interval can be obtained or, if it can, it does not reflect optimum hemodynamics. In one aspect of the present invention, an optimum AVD interval for pre-exciting the left ventricle in such patients may instead be computed from a linear function of the intrinsic delay between right atrial and left atrial activation, referred to as the RA-LA interval:

$$AVD = k_{11}(RA-LA) + k_{12}$$

where the AVD interval in this situation is the interval from an atrial event to a left ventricular pace. The coefficients of the equation may be obtained as before from a regression analysis of clinical population data. The technique may be implemented with the device in FIG. 1 using the right and left atrial sensing channels to measure the RA-LA interval as the interval between right atrial pace or sense and a left atrial sense. After obtaining the optimum AVD interval, the BVO interval may be set to either a nominal value or computed from intrinsic conduction data as described above.

Figure 2:
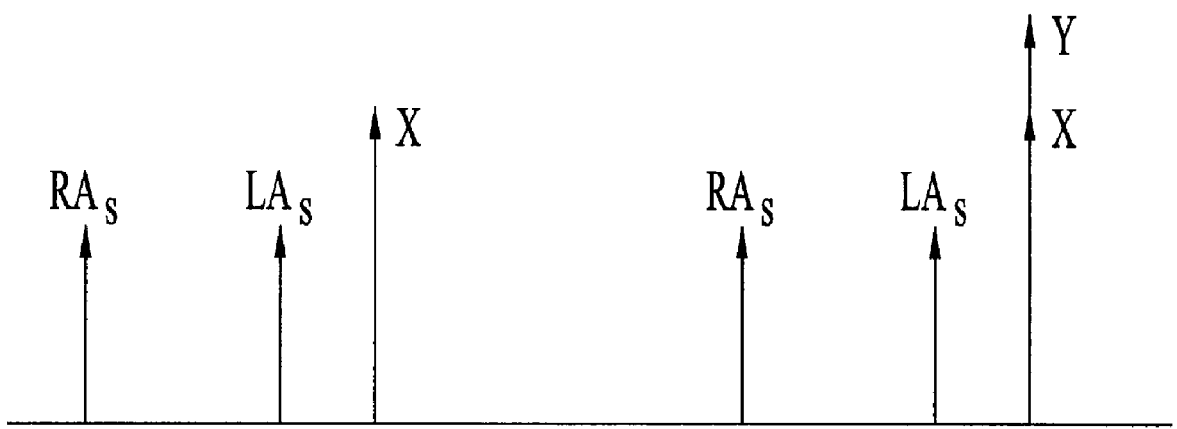
FIG. 2 is a timing diagram showing the relationship between the RA-LA interval and the programmed AVD interval.

The rationale for employing the RA-LA interval to compute an optimum AVD is as follows. When intrinsic depolarization is absent, intra-ventricular synchrony is optimized by delivering biventricular stimulation with or without an offset to result in septum-free wall fusion. Atrial-ventricular synchrony for the left atrium and left ventricle in this situation is optimized when the onset of left ventricular pressure rise coincides with the peak of left atrial contraction. To achieve optimal atrio-ventricular synchrony in the treatment of left ventricular dysfuction, stimulation to the left ventricle should therefore be applied at a certain time ahead of peak contraction in the left atrium. FIG. 2 is a timing diagram which illustrates this point. During an intrinsic beat, a right atrial sense $RA_S$ is followed by a left ventricular sense $LA_S$ which is then followed by the peak of left atrial contraction X. In a subsequent beat where the left ventricle is paced at an optimal AVD interval with respect to a right atrial sense, the left ventricular pace $LV_P$ results in the onset of left ventricular pressure rise Y coinciding with the peak of left atrial contraction X. The optimum AVD interval is thus proportional to the interval between the right atrial sense $RA_S$ and the peak of left atrial contraction X or its surrogate, the RA-LA interval between the right atrial sense $RA_S$ and the left atrial sense $LA_S$.

The RA-LA interval may also be used to compute optimal resynchronization parameters in patients with normal AV conduction. For example, if it is determined that intrinsic left ventricular activation occurs later than left atrial activation by a specified threshold amount, it may be desirable to compute the resynchronization pacing parameters based upon the intrinsic atrio-ventricular interval, the interventricular conduction delay, and the RA-LA interval. Thus, the right ventricle may be paced at an AVDR interval computed as described above as:

$$AVDR=k_5 AV_R + k_6 AV_L + k_7$$

or $$AVDR=k_3 AV_R + k_3 \cdot \Delta_{RL} + k_4.$$

The AVDL interval for pacing the left ventricle (or the BVO interval) may then be computed as a function of the RA-LA interval:

$$AVDL=k_{13}(RA\text{-}LA)+k_{14}.$$

5. CRT Pacing Configuration and Mode for Patients with Atrial Conduction Deficit In certain patients, an atrial conduction deficit exists such that left atrio-ventricular synchrony does not occur during intrinsic beats even if the intrinsic atrio-ventricular interval as measured from a right atrial sense to a right ventricular sense is normal. Another aspect of the present invention involves determining if such an atrial conduction deficit exists and adjusting pacing parameters accordingly. It may be implemented in an implantable device for delivering CRT such as illustrated in FIG. 1 which has sensing/pacing channels for both atria and both ventricles. In this embodiment, the implantable device is configured to deliver biventricular pacing in a manner specified by separate AVDR and AVDL intervals, where the AVDR interval is the delay between a right atrial event and a right ventricular pace and the AVDL interval is the delay between a right atrial event and a left ventricular pace. (The AVDR and AVDL parameters could, of course, be alternatively expressed in terms of an AVDR interval and a BVO interval as above.) An additional pacing parameter is also provided for pacing the left atrium, if necessary, referred to as the AAL interval which is an escape interval triggered by a right atrial event and results in a left atrial pace upon expiration. In order to optimally set the pacing mode and pacing parameters, the relative times of left atrial and left ventricular activation during an intrinsic beat are first determined. If the left atrium is depolarized later than the left ventricle by a specified threshold amount, or if the measured RA-LA interval is above a specified threshold amount, it can be surmised that a conduction deficit exists between the right and left atria. The device can therefore be configured to pace the left and right ventricles at AVDL and AVDR intervals calculated as described above from intrinsic conduction data (i.e., as a linear function of intrinsic AVD and $\Delta_{RL}$ intervals or intrinsic $AV_R$ and $AV_L$ intervals) and further configured to pace the left atrium at an AAL interval which is shorter than the AVDL interval by a specified offset.

Figure 3:
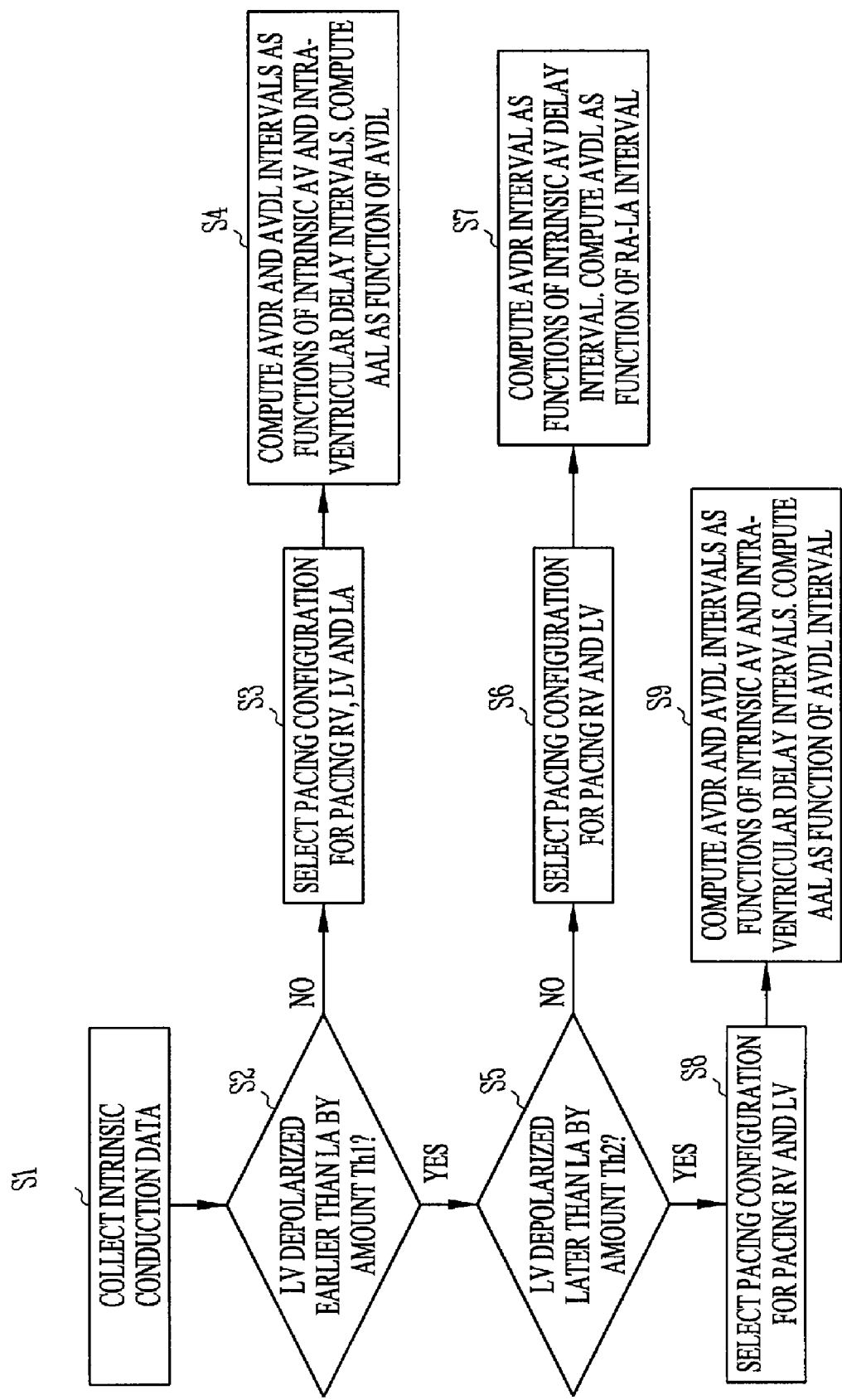
FIG. 3 illustrates an exemplary algorithm for setting pacing parameters.

6. Exemplary Algorithm for Computing Pacing Parameters and Setting Pacing Configuration FIG. 3 illustrates an exemplary algorithm which combines some of the techniques described above which may be used for a device capable of sensing/pacing both atria and both ventricles. At step S1, intrinsic conduction data is collected which reflect the intrinsic activation times of the four cardiac chambers. It is then determined at step S2 whether the left ventricle is depolarized earlier than the left atrium by a specified threshold Th1. If so, then a pacing configuration is selected at step S3 such that the right and left ventricles are stimulated and the left atrium is also stimulated. At step S4, the AVDR and AVDL delays are calculated from intrinsic atrio-ventricular and interventricular delay intervals, and the LA is stimulated with an AAL delay calculated as a function of the AVDL interval (e.g., such that AAL equals the AVDL delay plus/minus a variable offset). If the result at step S2 is negative, the algorithm proceeds to step S5 where it is determined whether or not the left ventricle is depolarized later than the left atrium by another threshold Th2. If so, then a pacing configuration is selected at step S6 in which only the left and right ventricles are paced. At step S7, the AVDL delay for pacing the left ventricle is calculated as a linear function of the RA-LA interval, and the AVDR interval for pacing the right ventricle is calculated from the intrinsic atrio-ventricular interval. If the result at step S5 is negative, a biventricular pacing configuration with no pacing of the left atrium is selected at step S8, and the AVDR and AVDL intervals are computed from the intrinsic atrio-ventricular and interventricular delay intervals at step S9.

7. Pacing Configuration for Pre-excitation of the Right Ventricle

Another aspect of the present invention relates to providing cardiac resynchronization therapy for right bundle branch block (RBBB) patients with or without LV dysfunction. Specifically, it relates to a pacing configuration and pacing parameter settings for improving RV hemodynamic function without compromising LV hemodynamic function. Currently, most CRT devices are mainly designed for treating HF patients with LBBB or other conduction disorders affecting the left ventricle, their aim being to improve LV hemodynamic function only. To achieve this goal, the electrode for pacing (and possibly sensing) the left ventricle is placed in proximity to left ventricular free wall, and the right ventricular electrode is placed in the right ventricle apex or in proximity to the ventricular septum. The two electrodes can then provide synchronous stimulation at both sides of the left ventricular chamber by, for example, simultaneously pacing the two sites or pre-exciting the left ventricular free wall. Research data have shown, however, that applying CRT with such a pacing configuration in RBBB patients, where the right ventricle is pre-excited relative to the left, can impair left ventricular hemodynamic function. One way that this effect may be partially ameliorated is by using a very long AVD interval to stimulate the right ventricle, but this approach still does not eliminate the deterioration of left ventricular hemodynamic function and, furthermore, does not provide optimal therapy to improve right ventricular hemodynamic function. A different placement for the right ventricular electrode (farther away from the left ventricle) with appropriately timed stimulation is proposed which improves right ventricular function with little or no impact on normal left ventricular hemodynamic function.

In accordance with the invention, cardiac resynchronization therapy is provided to a patient with a right ventricular conduction deficit with a first electrode disposed near the right ventricular free wall and a second electrode disposed near a cardiac site which is activated earlier than the right ventricular free wall during an intrinsic beat. The second electrode may be disposed, for example, in the right ventricular apex, near the right ventricular septum, or near the left ventricular free wall. In one embodiment, the right ventricular free wall is paced through the first electrode with a pacing mode such that a pacing pulse to the first electrode is triggered by a sense from the second electrode. In another embodiment, a third electrode is disposed in an atrium and an intrinsic atrio-ventricular interval AVI is measured from an atrial sense at the third electrode to a sense at the second electrode. The right ventricular free wall is then paced through the first electrode with an atrial tracking or AV sequential pacing mode such that a pacing pulse to the first electrode is delivered following an atrial event at an AV delay interval AVD, where the interval AVD is shorter than the measured atrio-ventricular interval AVI. In order to compute the AVD interval, this embodiment may further include delivering a pacing pulse to the first electrode, measuring a delay time D from the pacing pulse at the first electrode to a sense at the second electrode, and setting the AV delay interval AVD to be shorter than the measured atrio-ventricular interval AVI by the delay time D, i.e., $$AVD=AVI-D.$$

The pace to the first electrode should be delivered at an interval following an atrial event selected to be shorter than the intrinsic atrio-ventricular interval to the first electrode following an atrial event so that no intrinsic activation occurs.

In an example implementation, a first electrode is placed near the right ventricular free wall (preferably near the latest activated site), and a second electrode is placed in the right ventricular apex. The intrinsic atrio-ventricular interval from an atrial sense to a right ventricular sense at the apex is measured, designated as AVI. Next, the right ventricular free wall is stimulated at a very short AV delay interval AVD, and an interval D from the right ventricular pacing spike at the free wall to a right ventricular sense at the apex is measured. Resynchronization therapy is then provided by pacing the right ventricular free wall in an atrial tracking and/or AV sequential pacing mode with an AVD interval shorter than the measured intrinsic atrio-ventricular interval AVI by the measured interval D. That is, $$AVD=AVI-D.$$

In this manner, the right ventricular free wall is pre-excited so as to compensate for the RBBB and produce a synchronized right ventricular contraction without affecting normal left ventricular function.

In another example, a first electrode is placed near the right ventricular free wall, and a second electrode is placed near the right ventricular septum. The right ventricular free wall is then stimulated upon sensing at the right ventricular septum (in VVI mode), or with an AVD interval which is slightly less than the intrinsic AV interval between an atrial sense and a right ventricular sense at the septum (in VDD mode).

In another example, a first electrode is placed in the right ventricular free wall, and a second electrode is placed near the left ventricular free wall. The right ventricular free wall is stimulated upon sensing at the left ventricular free wall (in VVI mode), or with an AVD interval which is slightly less than the intrinsic AV interval between an atrial sense and the sense at the left ventricular free wall.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. An implantable cardiac rhythm management device, comprising:
    sensing channels for sensing cardiac activity in the right and left atria;
    one or more pacing channels for delivering paces to one or both ventricles;
    a controller for controlling delivery of the ventricular paces in an atrial tracking or AV sequential mode at a specified AVD interval following an atrial event;
    wherein the controller is further programmed to measure the interval from a right atrial sense or pace to a left atrial sense, designated as the RA-LA interval; and,
    means for computing an optimum value for the AVD interval as a linear function of the measured RA-LA interval.

2. The device of claim 1 wherein the optimal value of the AVD interval is computed as:

$$AVD=k_{11}(RA\text{-}LA)+k_{12}$$

where the coefficients $k_{11}$ and $k_{12}$ defining the relationship between the optimum AVD interval and the measured RA-LA interval are derived from a linear regression analysis of clinical population data relating measured RA-LA intervals to an optimum AVD interval for delivering cardiac resynchronization therapy as determined by measurement of a cardiac function parameter.

3. The device of claim 1 wherein the optimum AVD interval computing means is the controller.

4. The device of claim 1 wherein the optimum AVD interval computing means is an external programmer in communication with the controller.

5. An implantable cardiac rhythm management device, comprising:
    atrial sensing channels for sensing cardiac activity in the right and left atria;
    ventricular pacing channels for delivering paces to the right and left ventricles;

a controller for controlling delivery of paces through the ventricular pacing channels in a biventricular pacing mode where paces are delivered to the right and left ventricles following an atrial event in an atrial tracking or AV sequential pacing mode at AV delay intervals designated as AVDR for the right ventricle and AVDL for the left ventricle;

wherein the controller is programmed to measure an intrinsic atrio-ventricular interval $AV_R$ as the interval from an atrial event to a right ventricular sense;

wherein the controller is programmed to measure an intrinsic atrio-ventricular interval $AV_L$ as the interval from an atrial event to a left ventricular sense;

wherein the controller is programmed to measure the interval from a right atrial event to a left atrial sense in the patient, designated as the RA-LA interval;

means for computing optimal values for the AVDR and AVDL intervals as linear functions of the $AV_R$, $AV_L$, and/or RA-LA intervals.

6. The device of claim 5 wherein the optimal AVDR and AVDL computing means computes the optimal values by:

determining the relative times at which the left atrium and left ventricle are activated during an intrinsic beat;

if it is determined that intrinsic left ventricular activation occurs later than left atrial activation by a specified threshold amount, computing the resynchronization pacing parameters as:

$$AVDR = k_5 AV_R + k_6 AV_L + k_7$$

and $$AVDL = k_{13}(RA\text{-}LA) + k_{14}$$

where $k_5$, $k_6$, $k_7$, $k_{13}$, and $k_{14}$ are specified coefficients; and, if it is determined that intrinsic left ventricular activation does not occur later than left atrial activation by the specified threshold amount, computing the resynchronization pacing parameters as:

$$AVDR = k_5 AV_R + k_6 AV_L + k_7$$

and $$AVDL = k_8 AV_R + k_9 AV_L + k_{10}$$

where $k_5$ through $k_{10}$ are specified coefficients.

7. The device of claim 5 wherein the optimum AVDR and AVDL computing means is the controller.

8. The device of claim 5 wherein the optimum AVDR and AVDL computing means is an external programmer in communication with the controller.

9. The device of claim 5 wherein the specified coefficients for computing the optimum values for the AVDR and AVDL intervals are derived from a linear regression analysis of clinical population data relating a measured intrinsic interval to an optimum AVDR and AVDL value for delivering cardiac resynchronization therapy as determined by measurement of a cardiac function parameter.

10. An implantable cardiac rhythm management device, comprising:

atrial sensing channels for sensing cardiac activity in the right and left atria;

ventricular pacing channels for delivering paces to the right and left ventricles;

a controller for controlling delivery of paces through the ventricular pacing channels in a biventricular pacing mode where paces are delivered to the right and left ventricles following an atrial event in an atrial tracking or AV sequential pacing mode at AV delay intervals designated as AVDR for the right ventricle and AVDL for the left ventricle;

wherein the controller is programmed to measure an intrinsic atrio-ventricular interval $AV_R$ as the interval from an atrial event to a right ventricular sense;

wherein the controller is programmed to measure an intrinsic atrio-ventricular interval $AV_L$ as the interval from an atrial event to a left ventricular sense;

means for computing optimal pacing parameters by:

determining the relative times at which the left atrium and left ventricle are activated during an intrinsic beat;

computing the optimal values for the AVDR and AVDL intervals as:

$$AVDR = k_5 AV_R + k_6 AV_L + k_7$$

and $$AVDL = k_8 AV_R + k_9 AV_L + k_{10}$$

where $k_5$ through $k_{10}$ are specified coefficients; and, if it is determined that intrinsic left atrial activation occurs later than left ventricular activation by a specified threshold amount, computing a parameter for pacing the left atrium at an escape interval triggered by a right atrial event, referred to as the AAL interval, as a value shorter than the computed AVDL interval by a specified offset.

11. The device of claim 10 wherein:

the controller is further programmed to measure the interval from a right atrial sense or pace to a left atrial sense in the patient, designated as the RA-LA interval; and the optimal pacing parameter computer means is further configured to determine if the RA-LA interval exceeds a specified threshold amount and, if so, to compute a parameter for pacing the left atrium at an escape interval triggered by a right atrial event, referred to as the AAL interval, as a value shorter than the computed AVDL interval by a specified offset.

12. The device of claim 10 wherein the optimum pacing parameter computing means is the controller.

13. The device of claim 10 wherein the optimum pacing parameter computing means is an external programmer in communication with the controller.

14. The device of claim 10 wherein the specified coefficients for computing the optimum pacing parameter values are derived from a linear regression analysis of clinical population data relating a measured intrinsic interval to an optimum pacing parameter value for delivering cardiac resynchronization therapy as determined by measurement of a cardiac function parameter.

* * * * *